United States Patent [19]

Baugh

[11] Patent Number: 5,574,230
[45] Date of Patent: Nov. 12, 1996

[54] SILICA GEL, TENAX, AND CARBON MEDIA ADSORPTION TUBE FOR THE SAMPLING OF A WIDE VARIETY OF ORGANIC COMPOUNDS IN AIR AND GAS STREAMS

[75] Inventor: Steven F. Baugh, Broomfield, Colo.

[73] Assignee: Havelick & Associates, Ltd., Broomfield, Colo.

[21] Appl. No.: 326,594

[22] Filed: Oct. 20, 1994

[51] Int. Cl.$^6$ .................................................. G01N 1/22
[52] U.S. Cl. .................................. 73/863.23; 73/863.21
[58] Field of Search ............................ 73/863.23, 863.21

[56] References Cited

U.S. PATENT DOCUMENTS

| | | | |
|---|---|---|---|
| 4,040,805 | 8/1977 | Nelms et al. | 73/31.03 X |
| 4,180,389 | 12/1979 | Paul | 95/11 |
| 4,698,071 | 10/1987 | Elias | 95/109 |
| 4,759,210 | 7/1988 | Wohltjen | 73/31.07 |
| 4,977,095 | 12/1990 | Zaromb | 73/864.81 X |
| 5,081,871 | 1/1992 | Glaser | 73/863.23 |
| 5,137,744 | 8/1992 | Cagley et al. | 426/615 |
| 5,370,004 | 12/1994 | Bossart et al. | 73/863.23 |

*Primary Examiner*—Thomas P. Noland

[57] ABSTRACT

An air sampling tube containing silica gel, Tenax, and carbon is used to sample air containing either unknown contaminants or a mixture of a wide variety of organic compounds, varying in boiling points, functionality and overall polarity. The sampling tube presented here, HAL1, is only one of several possible tube configurations utilizing a variety of adsorption materials in differing combinations, amounts, and different sampling devices or methods. HAL1 is prepared and assembled in a common configuration similar to the (EPA TO-1) configuration for thermal desorption and subsequent analysis by GC/MS. Thermal desorption eliminates solvent extractions and deposits the entire sample in the instrument for increased method sensitivity while eliminating solvent peak fronts from masking low level analytes which coelute. This sample collection tube will allow rapid collection and analysis of a wide variety of organic compounds, affording subsequent analysis by an appropriate analytical technique using commercially available thermal desorption tube sample introduction systems.

1 Claim, 1 Drawing Sheet

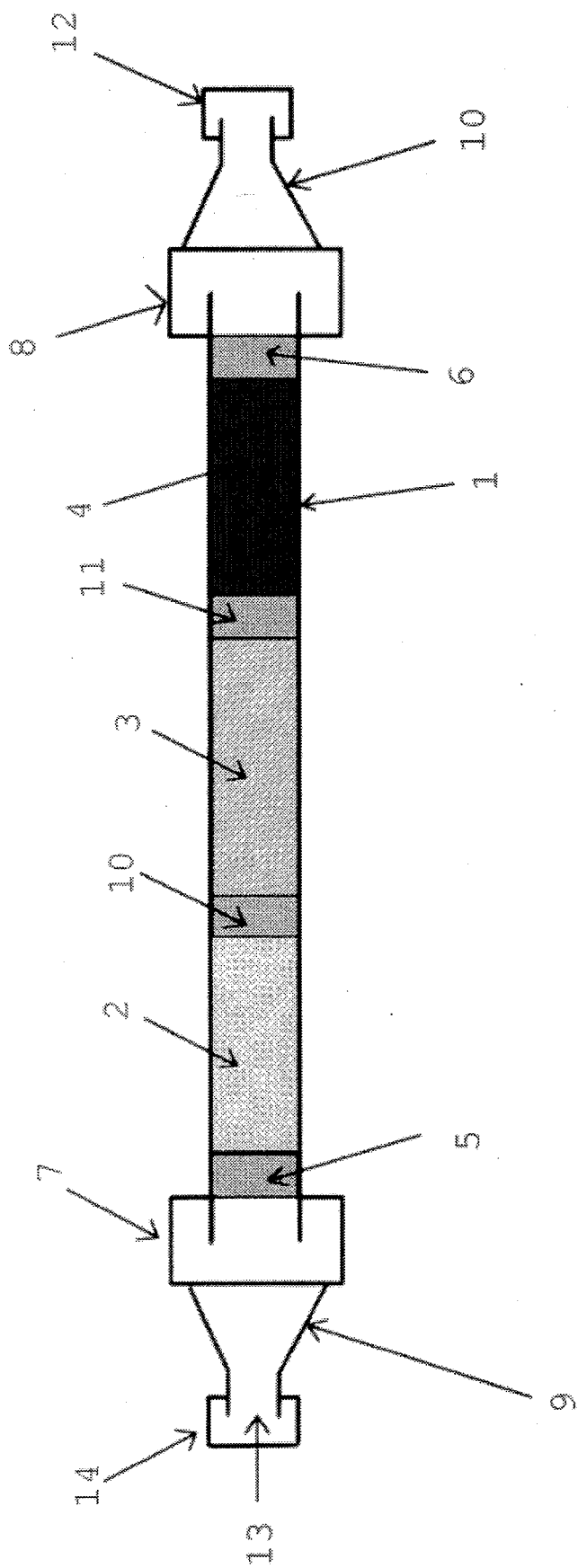

SILICA GEL, TENAX, AND CARBON MEDIA ADSORPTION TUBE FOR THE SAMPLING OF A WIDE VARIETY OF ORGANIC COMPOUNDS IN AIR AND GAS STREAMS

SUMMARY OF INVENTION

The merits of silica gel, Tenax, and carbon are well established as adsorption media for use in air sampling tubes, each with their own advantages [1,2,3,4]. When used in combination sample collection of widely differing compounds from methanol to petroleum naphtha is possible with a single sample tube and one subsequent analysis, eliminating possibly two additional sample collections and two additional subsequent analyses. As will be understood by those of ordinary skill in the art, the invention is applicable in a wide variety of applications, including for example, indoor air quality sampling, industrial hygiene sampling, industrial process sampling, stack emission sampling, soil gas sampling, clean air act monitoring, personnel monitoring, emissions sampling, ambient air sampling, pollution control monitoring, environmental sampling, and exhaust gas sampling.

Using thermal desorption for sample release from the media eliminates the need for familiar extraction solvents and their associated concerns. The entire sample is introduced into the GC/MS or other instrument, raising the analytical sensitivity of the method in comparison to extraction sample release methods where only small aliquots of the entire sample are introduced into the instrument.

Traditionally carbon adsorption tubes have been eluted with carbon disulfide and analyzed on a GC using a Flame Ionization Detector (FID)[1,2,3,4]. This method creates costs associated with purchase of the solvent, hazards of storage and handling, cost of extraction in labor and additional materials. Overall method sensitivity is compromised in the traditional methods since only a portion of the sample is analyzed. Extraction also introduces additional errors associated with sample aliquoting and physical sample loss.

With the variety and specialization of chemicals available in business, industry, and the home, analyses using an instrument such as the GC/Mass Spectrometer (GC/MS) are possible with thermal desorption. GC/MS offers positive identification of sample components and accurate concentration determinations with calibrated response factors for each component.

Time and costs associated with sampling and analysis are reduced greatly for unknown determinations or determinations of complex mixtures of interest. Combining multiple media in a single tube makes the cost of such determinations using GC/MS comparable to or less than three or more sampling and analysis events. At the same time the HAL 1 method offers more information and more accurate quantitation. This method allows rapid determination of components and concentrations in complex mixtures and unknown situations, and allows useful application of GC/MS to compounds of interest not available before.

BRIEF DESCRIPTION OF THE DRAWING

The sole drawing figure, attached, depicts a tube design similar to the typical design gaining wide spread use for thermal desorption of air sampling adsorption media (TO-1) and subsequent GC/MS analysis but containing a novel combination and arrangement of sample collecting elements. The drawing shows elements which, per se, are similar to those typically used in phase separation in air sampling tubes. Use of the metal desorption tubes simplifies handling and avoids contamination released during desorption common to compression fit thermal desorbers.

DETAILED DESCRIPTION

The example in Figure One shows a glass wool plug 5 and 150 mg silica gel 2 at the entrance or inlet 13 of the tube 1, allowing adsorption of polar components and water vapor which could reduce adsorption efficiencies downstream. The tube is preferably a stainless steel tube having a 12.7 mm outer diameter and being 100 mm long. The use of silica gel as the first phase dries the air before the Tenax (an absorbent polymer of, or derivitative of, 2,6-diphenyl-p-phenylene oxide) or carbon phases shown respectively as elements 3 and 4 in the tube, since both Tenax and carbon have adsorption efficiencies which can be influenced significantly by water vapor[4]. 500 mg of Tenax is shown separated from the silica gel by glass wool plug 10, with another glass wool plug 11 separating the 150 mg carbon and the Tenax. A final glass wool plug 6 is at the tube end. The opposing ends of tube 1 are each connected to a fitting connected to a reducer connected to an end cap. To collect a sample, inlet end cap 14 is removed, allowing gas to pass in order through inlet 13, a passage through ½" to ⅛" reducer 9, and a passage in fitting 7 and into tube 1. Fitting 7 is generally similar to ½" Swagelok fitting 8 at the opposite end of the tube. Reducer 10, generally similar to reducer 9, interconnects fitting 8 and end cap 12.

TUBE PREPARATION:

Silica gel, Tenax, and carbon media preparation procedures are well documented, and each should be prepared according to established methods, with emphasis placed on reducing solvent contamination during handling and storage[1,2,3,4]. The tube should be assembled using glass wool plug ends and separations of media, utilizing any combination of media varieties, quantities and placements in the air sampling tube.

In the example presented here, the HAL1 tube will be thermally desorbed at a maximum temperature of 300° C., so the assembled tube should be heated and purged at a minimum of 300° C. prior to the ends being capped. Stainless Steel tubes of this design are reusable following a bake and purge cycle. Engraved markings of tube identifiers to avoid contamination markings are encouraged, along with marking the inlet side of the tube. Tubes should be stored for transportation in solvent free freezers, using friction seal protective outer containers.

SAMPLE COLLECTION:

After setting up the sampling apparatus necessary, including possibly pre-filters and sodium sulfate for non-adsorption drying of excess water vapor, the tube should be removed from the shipping container. Proper sampling procedures are well established and should be performed within two weeks of tube preparation[1]. The tube is re-sealed and placed in the protective outer container and placed in a solvent free freezer as soon as possible. Sample analysis should be completed within two weeks of sampling.

Tubes of this design can handle sample flow volumes between 20 and 500 ml/minute. Because of media volume reduction to accommodate three phases, two tubes must be used in series to monitor break through, and care must be taken not to overload the sampling tubes, typically require collection volumes of less than 10 liters. Proper determination of adsorbent amount, flow rate, and total sample volume will require calculations based on adsorption capacities, adsorption efficiencies, and expected concentrations or regulatory levels.

SAMPLE ANALYSIS:

Thermal desorption of the example air sampling tube HAL1 can be directly into the GC/MS, or other appropriate instrument, or collected on a sample introduction system trap of the same phases, silica gel, Tenax, and carbon[5]. Care must be taken not to exceed the capacity of a purge and trap collection trap of smaller size and media volumes. Proper analytical conditions and parameters are to be determined with each sampling event, tube design, and construction.

QUALITY ASSURANCE:

References to established methodologies and procedures are used throughout the monograph and incorporate a great deal of method development and statistical review[1,2,3,4,5]. References to sample contamination and storage cannot be over stressed, as media contamination and sample loss are the largest sources of error for these methods.

REFERENCES (EACH OF THE FOLLOWING REFERENCES ARE HEREBY INCORPORATED BY REFERENCE IN THEIR ENTIRETY):

1. EPA-600/4-84-041, "Compendium of Methods for the Determination of Toxic Organic Compounds in Ambient Air", methods TO-1, TO-2, April, 1984.
2. NIOSH "Manual of Analytical Methods", third edition, methods 1501, 2000, 1984.
3. OSHA "Analytical Methods Manual", CIM method, 1985.
4. ASTM, "1989 Annual Book of ASTM Standards", method D 3686–89, 1989.
5. Supelco, purge trap c for Tekmar, containing silica gel, Tenax, and carbon, part number 2-1061.

I claim:

1. A method for sampling gas wherein said method comprises providing a sample tube comprising silica gel, an adsorbent polymer of, or derivative of, 2,6-diphenyly-p-phenylene oxide, and carbon, said sample tube comprising a stainless steel tube having a glass wool plug at opposite ends thereof, each end connected to a fitting connected to a reducer connected to an end cap, one said end cap being an inlet end, the method further comprises removing the cap at the inlet end such that gas being sampled can pass into the stainless steel tube by passing in order through a passage in the reducer at the inlet end, a passage in the fitting at the inlet end, and the glass wool plug at the inlet end, and wherein the silica gel, adsorbent polymer of, or derivative of, 2,6-diphenyl-p-phenylene oxide, and carbon are located within the stainless steel tube and arranged therewithin such that after passing through the glass wool plug at the inlet end the gas being sampled can pass in order through the silica gel, a glass wool plug, the adsorbent polymer of, or derivative of, 2,6-diphenyl-p-phenylene oxide, a glass wool plug, the carbon, and the glass wool plug at the end of the stainless steel tube opposite the inlet end.

* * * * *